US006943902B2

(12) United States Patent
Borchardt et al.

(10) Patent No.: US 6,943,902 B2
(45) Date of Patent: Sep. 13, 2005

(54) METHOD FOR THE QUALITY CONTROL OF MATERIAL LAYERS

(75) Inventors: Michael Borchardt, Neuenkirchen (DE); Frank Wendzinski, Telgte (DE); Dorthe Eikermann, Münster (DE)

(73) Assignee: Institut Für Chemo-Und Biosensorik Münster E.V., Münster (DE)

( * ) Notice: Subject to any disclaimer, the term of this patent is extended or adjusted under 35 U.S.C. 154(b) by 218 days.

(21) Appl. No.: 10/148,992

(22) PCT Filed: Dec. 1, 2000

(86) PCT No.: PCT/EP00/12105

§ 371 (c)(1),
(2), (4) Date: Jun. 6, 2002

(87) PCT Pub. No.: WO01/42772

PCT Pub. Date: Jun. 14, 2001

(65) Prior Publication Data

US 2002/0180992 A1 Dec. 5, 2002

(30) Foreign Application Priority Data

Dec. 6, 1999 (DE) .......................................... 199 58 641

(51) Int. Cl.[7] .............................................. G01B 11/06
(52) U.S. Cl. ....................................... 356/632; 356/630
(58) Field of Search ................................. 356/630, 632, 356/625, 239.1, 239.3, 237.2, 237.5; 250/559.27, 559.28

(56) References Cited

U.S. PATENT DOCUMENTS 4,302,108 A * 11/1981 Timson ........................ 356/450
5,416,594 A    5/1995 Gross et al.
5,673,028 A * 9/1997 Levy ............................ 340/635

FOREIGN PATENT DOCUMENTS

| DE | 197 07 645.9 | 8/1998 | |
|----|--------------|--------|--|
| EP | 0 230 365 B1 | 7/1987 | |
| EP | 0 693 682 A2 | 1/1996 | |
| EP | 0 776 257 B1 | 6/1997 | |
| EP | 0 838 850 A2 | 4/1998 | |
| EP | 0838850 A2 * | 4/1998 | ........... H01L/21/66 |
| WO | WO 98/18135 | 4/1998 | |

OTHER PUBLICATIONS

PCT International Preliminary Examination Report for PCT/EP00/12105, filed Dec. 1, 2000.

* cited by examiner

Primary Examiner—Gregory J. Toatley, Jr.
Assistant Examiner—Roy M. Punnoose
(74) Attorney, Agent, or Firm—Leydig, Voit & Mayer, Ltd.

(57) ABSTRACT

Disclosed is a method for quality control of a material layer, which involves providing the material of the layer with an agent for absorbing an electromagnetic radiation, irradiating the surface of the layer with an electromagnetic radiation, and measuring the amount of light emitted by the material layer, for example, reflected radiation or fluorescence radiation.

14 Claims, 6 Drawing Sheets

METHOD FOR THE QUALITY CONTROL OF MATERIAL LAYERS

BACKGROUND OF THE INVENTION

1. Field of the Invention

The present invention relates to a method for the quality control of material layers. Methods of this type are used in particular in quality control and quality assurance of articles which can be mass-produced.

2. Description of the Related Art

According to WO 98/18135, the quality of a coating is checked by light being radiated onto the coating and the transmitted light being detected. From the transmission or respectively the absorption of the light as it passes through the coating, conclusions are made about local or overall defects in the coating.

U.S. Pat. No. 4,302,108 discloses a method in which a coating is also scanned with a light beam. What is crucial here is that the angle of radiation onto the coating is so selected that at least a portion of the beam is reflected. The intensity of the reflected beam is then detected in order to determine surface anomalies of the structure. By means of this method, which is substantially based on an angle of radiation which leads to a reflection at the surface of the coating, surface defects of the coating can be detected. These described methods relate to planar surfaces.

BRIEF SUMMARY OF THE INVENTION

Proceeding from this prior art, the object of the present invention is to make available a method for the quality control of material layers, by means of which the quality of the layer can be measured in a non-destructive manner in respect of layer thickness and surface defects, simply, quickly and cost-effectively.

This object is accomplished by the method according to the preamble of claim 1 in conjunction with its characterising features. Furthermore, fields of use of the method are quoted in claims 11 and 12.

BRIEF DESCRIPTION OF THE DRAWINGS

Some examples of the method according to the invention are given below. The figures show.

DETAILED DESCRIPTION OF THE INVENTION

Figure 1:
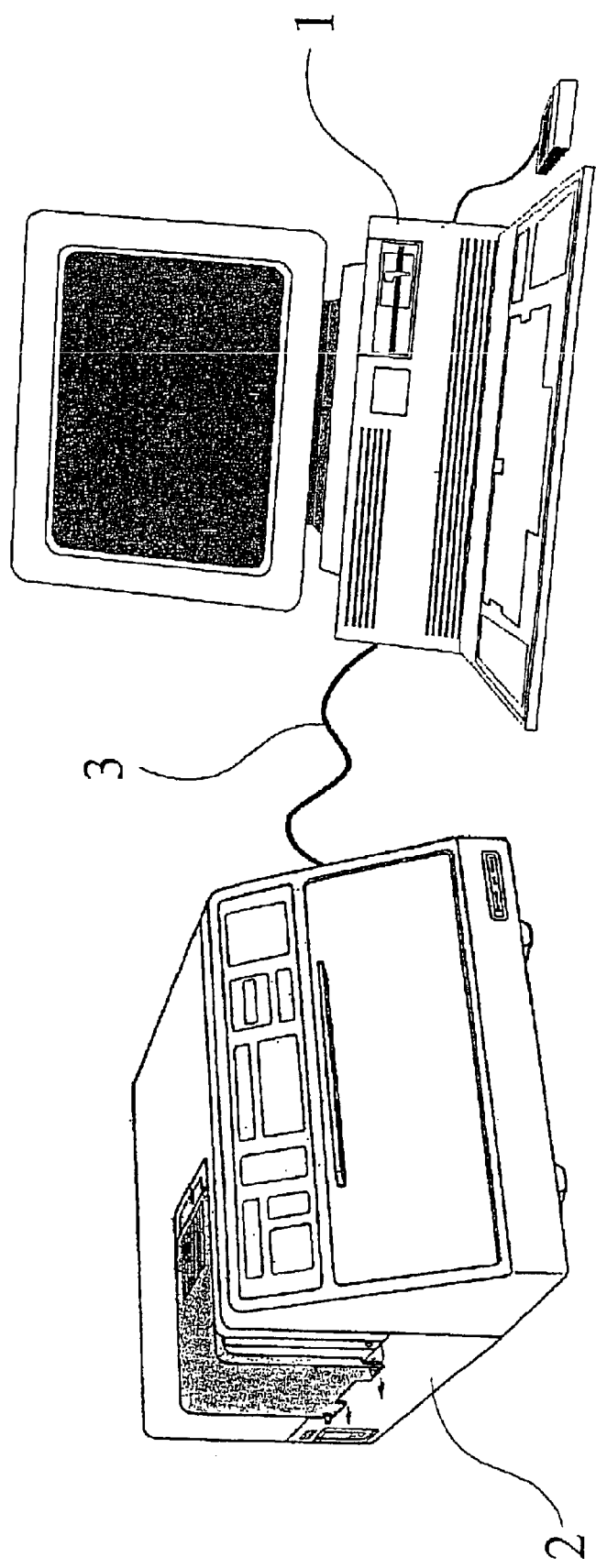
FIG. 1 a measuring arrangement for a method according to the invention.

Advantageous developments of the method according to the invention are given by the dependent claims.

The invention proceeds from a method according to U.S. Pat. No. 4,302,108, in which a specific angle of irradiation has to be observed in order to generate reflected radiation. Differing from this, however, the present invention proceeds from the material of the layer to be examined being provided with an agent which absorbs electromagnetic radiation (absorber), for example a colouring or fluorescent agent, and the light then reflected from the material or emitted as fluorescent light is measured. Here the light, which after penetration into the layer is reflected in deeper planes of the layer and/or fluoresced and for example leaves the layer again via the surface, is also detected. The present invention exploits first of all the fact that the reflectivity is dependent on the absorption capacity of the respective material and therefore the luminance factor of the material depends on its absorption coefficient. In this way it becomes possible also to measure layer materials which for example for their part do not have any substantial inherent absorption in the ultraviolet or visible light ranges. Nevertheless, by colouring the material with an agent which absorbs electromagnetic radiation, absorption can be created and thus the luminance factor can be increased independently of the angle of irradiation.

As agents which absorb electromagnetic radiation can be considered colorants, e.g. colouring agents such as dyes or pigments, or also agents which absorb electromagnetic radiation such as UV absorbers or fluorophores.

In the case of the use of a fluorophore, it is not the radiation emitted by scattering from the surface but the fluorescent light of the layer emitted over the surface which is determined. Both processes, the determination of the back-scattered portion or of the fluorescent light, are equally suitable for the present method.

Through the method according to the invention, a generally usable, quick and cost-efficient on-line quality control is possible, for example for surfaces which can be mass-produced. This method is non-destructive and non-contact and can be used to determine layer thicknesses or also surface defects or irregularities. Thus consequently amounts of filling, layer thickness distributions, defects such as holes, accumulation or inhomogeneities can be detected in any materials. The method is particularly advantageously suitable for the quality control and quality assurance of plastics membranes, polymer membranes, in particular ion-selective membranes or hydrogels or the like.

Such plastics membranes are used for example in ion-selective electrodes for biosensors.

With the method according to the invention, not only membranes but also hydrogels can be examined. If the colouring agent necessary for the densitometric measurement is not to be dissolved out of the membrane in this process, it must be bound to particles. These particles are in turn enclosed by the hydrogel. Latex particles are particularly suitable as such particles.

The layer can advantageously be scanned point-by-point, it being possible for the scanning to take place in a specific direction. By this means it is possible, for example, to measure in sequence a linear arrangement of ion-selective electrodes in respect of their membrane layer thickness. In particular the incorporation of the method for quality control according to the present invention in a sequential production cycle is possible.

Since the luminance factor or respectively the fluorescence of a material depends on its absorption coefficient, the luminance factor or the fluorescence is also bound to the wavelength of the incident light. It is advantageous, therefore, if the electromagnetic radiation radiated onto the layer has a wavelength which corresponds to an absorption band of the absorber. However it should be borne in mind here that, via the choice of the irradiated wavelength or the choice of the colorant concentration in the membrane, a measurement is taken in a region in which a clearly evaluable relationship, ideally a linear relationship, arises between the amount of reflected light or respectively fluorescent light and the layer thickness of the membrane.

Particularly suitable for the present method are the colouring agents curcumin (1,7-bis(4-hydroxy-3-methoxyphenyl) 1,6-heptadiene-3,5-dione), scarlet red (1(-2-methyl-4-o-tolylazo-phenylazo)-2(naphthol), or Sicodop blue (pigment paste, trade name of an insoluble colorant produced by the company BASF, chemical structure not made public). Curcumin is a fluorescent colorant which has the additional advantage of being non-toxic as a food colorant.

FIG. 1 shows an arrangement for measuring according to the method of the invention. This arrangement has a computer 1 and a TLC scanner 2 (thin-layer chromatography scanner) as a densitometer. The TLC scanner 2 and the computer 1 are connected via a connecting cable 3, via which the computer controls the densitometer 2 and records the measurement curves.

For measuring, the object to be measured is positioned on the bed of the scanner 2, fixed with magnetic strips and inserted into the densitometer 2. For measurements in the visible light range, a tungsten lamp is used as the light source, whilst a mercury lamp is selected to stimulate fluorescence. In the latter case, in addition a corresponding cut-off filter must be positioned before the measuring photomultiplier of the densitometer 2, in order to separate spectrally excitation light and fluorescent light.

Figure 2:
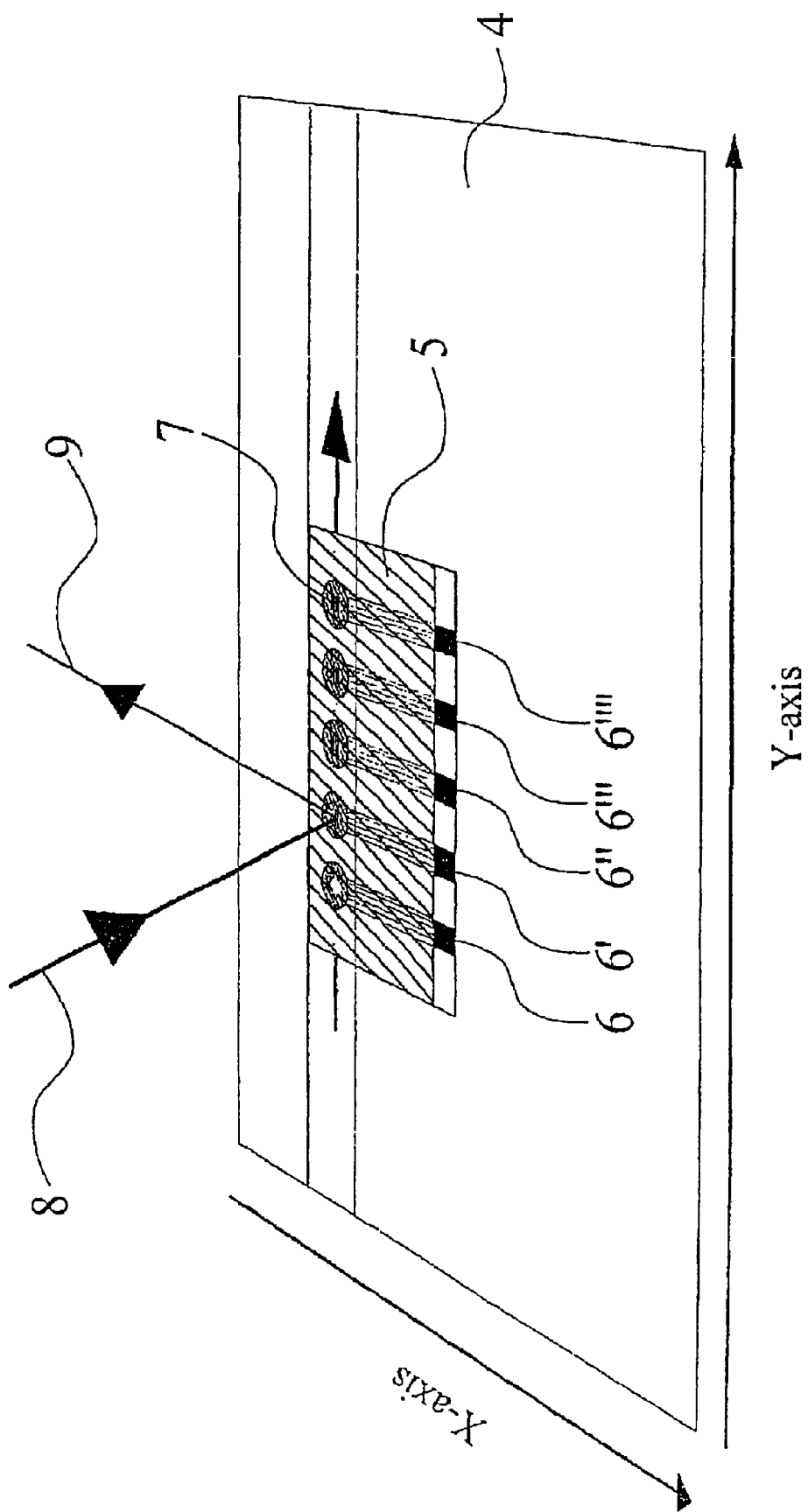
FIG. 2 the method according to the invention.

After input of the corresponding measuring parameters into the computer 1, the measurement begins. The light beam travels in one direction over the sample, as represented in FIG. 2. The intensity of the reflected light is measured and is represented as absorption on the basis of its proportionality to the absorption. Alternatively the fluorescent light is measured.

FIG. 2 shows the measurement of a sequence of ion-selective electrodes.

To produce ion-selective electrodes of this type, plastics membranes with intercalary analyte-specific ionophores are used. In the case of sensors which are produced in double-matrix membrane technology, a PVC membrane is, for example, applied in liquid form to a porous material. A portion of the membrane penetrates into the matrix, the remainder is uniformly distributed over the porous layer in a cavity. In this process, the electrode is sealed against the measuring medium. In order to minimise leaks, according to the present state of knowledge, an at least four-fold filling of the electrode with PVC cocktail is necessary. Maintaining the quality requirement of uniformity of the filling and impermeability is then checked with the densitometric method according to the invention. To this end, a corresponding colouring or fluorescent agent, for example, which absorbs electromagnetic radiation, is added to the PVC membrane in the liquid state, before it is poured. As absorbent substances can be considered the above-mentioned pigments or colorants. Furthermore, fluorophores can be used.

FIG. 2 now shows a sequence of ion-selective electrodes 6, 6', 6'', 6''', 6'''', mass-produced in this way, which are disposed on a measuring table 4. The electrodes are produced as individual sensor strips in a sensor array 5 and are disposed the one beside the other. The electrodes 6 to 6'''' each have a measuring head 7. This measuring head 7 contains the ion-selective membrane to be measured.

Excitation light 8 is now radiated onto the measuring table and the light 9 reflected from the measuring heads 7 is then measured and represented as absorption. Via the amount of reflected light, the layer thickness and also the homogeneity of the ion-selective membrane in the measuring heads 7 is thus scanned.

The measuring table 4 is displaced in the direction of the arrow, such that on the one hand the individual sensor strips are measured in the sequence 6'''', 6''', 6'', 6' and finally sensor strip 6, and on the other hand, the profile of the ion-selective membrane of each individual measuring head 7 is also determined in the direction of the arrow.

In order to adjust the measuring range of the densitometer, before measurement a null balance is carried out with an uncoloured matrix.

Figure 3:
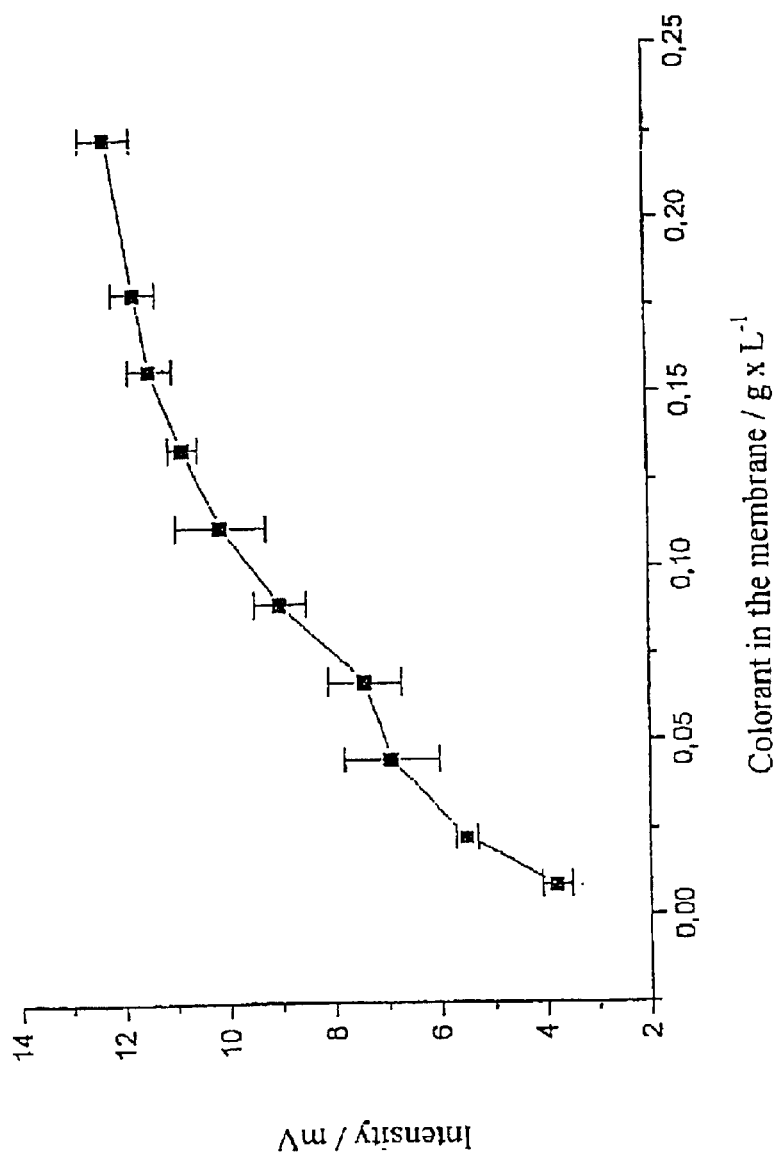
FIG. 3 the correlation between colorant concentration and signal intensity.

FIG. 3 shows a calibration curve for electrode membranes of the type described, with different concentrations of the colorant scarlet red. Up to a concentration of approximately 0.12 g/l scarlet red in the membrane, can be recognised an extra linear interdependency of intensity and amount of colorant in the membrane. In order, within the framework of quality assurance, to be able to distinguish well between different membrane thicknesses, the attained amount of colorant should, with a sufficient filling of the membrane cavity of the measuring heads 7, lie below this concentration at least by a factor of 2. In the case of higher concentrations, one leaves the linear measuring range and the resolution of the measurement is poorer, if not impossible.

Figure 4:
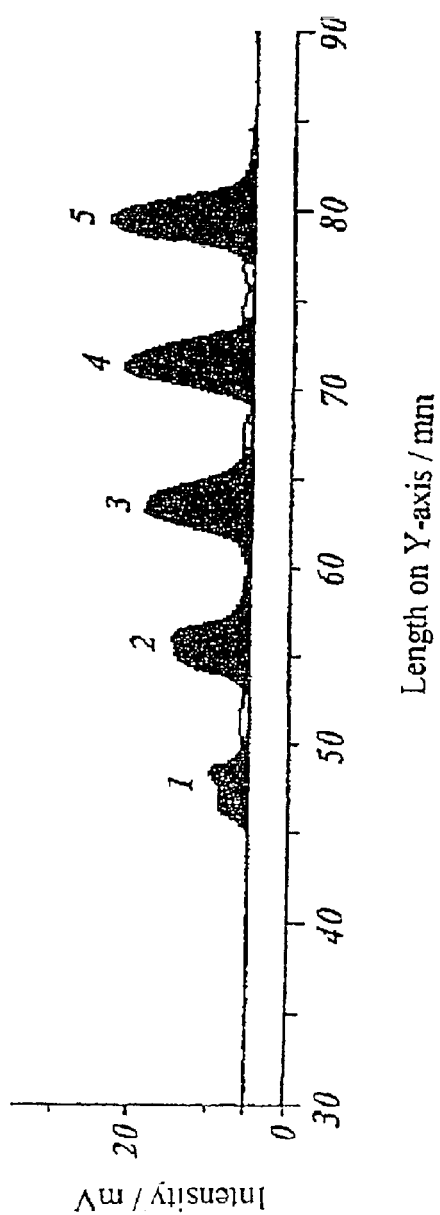
FIG. 4 the correlation between membrane layer thickness and intensity of the signal for the colouring agent scarlet red.

FIG. 4 shows a measuring curve which has been determined according to a method as shown in FIG. 2, on five consecutive measuring heads 7. The individual measuring heads have here been filled once (reference numeral 1) twice (reference numeral 2), three times, four times or five times (reference numerals 3, 4 or 5 respectively) with an ion-selective membrane, which contained 0.0224 g/l scarlet red. On the basis of the fixed cavity dimensions for the ion-selective membrane, measuring heads with five different layer thicknesses of the ion-selective membrane were produced in this way.

As can be immediately recognised, with the same colorant concentration in the ion-selective membrane, the layer thickness results in five different signal intensities, the signal intensity correlating directly with the layer thickness. This provides the proof that the method according to the invention can be used to determine layer thicknesses in ion-selective membranes.

Figure 5:
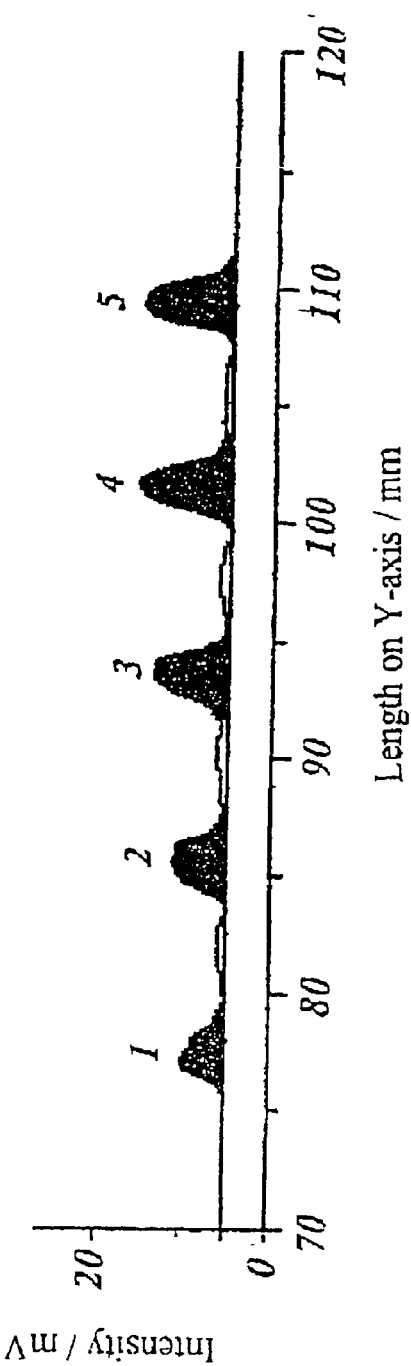
FIG. 5 the relationship between membrane layer thickness and intensity of the signal for the fluorescent colouring agent curcumin, and FIG. 6 signals from the measurement of two ion-selective electrodes.

FIG. 5 shows a further measuring curve which has been determined according to a method as shown in FIG. 2, on five consecutive measuring heads 7. The individual measuring heads were here filled once to five times (reference numerals 1 to 5) with an ion-selective membrane, which contained 0.0224 g/l curcumin. In this way, five measuring heads were produced, the membrane layer thicknesses of which vary between the single original layer thickness and five times the original layer thickness in measuring head 1. As can be immediately recognised, here too, with the same colorant concentration in the ion-selective membrane, the layer thickness results in five different signal intensities for the measured fluorescent radiation, the signal intensity for measuring heads 1 to 4 correlating with the layer thickness. The signal intensity between measuring head 4 and measuring head 5 no longer differs substantially, since here the saturation region of the signal has been reached as a result of the large layer thickness. The colorant curcumin can consequently be used in the selected concentration of 0.0224 g/l in order to distinguish the layer thicknesses of measuring heads 1 to 4 from one another. In order also to correspondingly detect larger layer thicknesses, such as those of measuring head 5 for example, a reduction of the concentration of the fluorescent colorant curcumin in the membrane solution would be necessary. This provides the proof that the method according to the invention can also be used via the detection of fluorescent light to determine layer thicknesses in ion-selective membranes.

Figure 6:
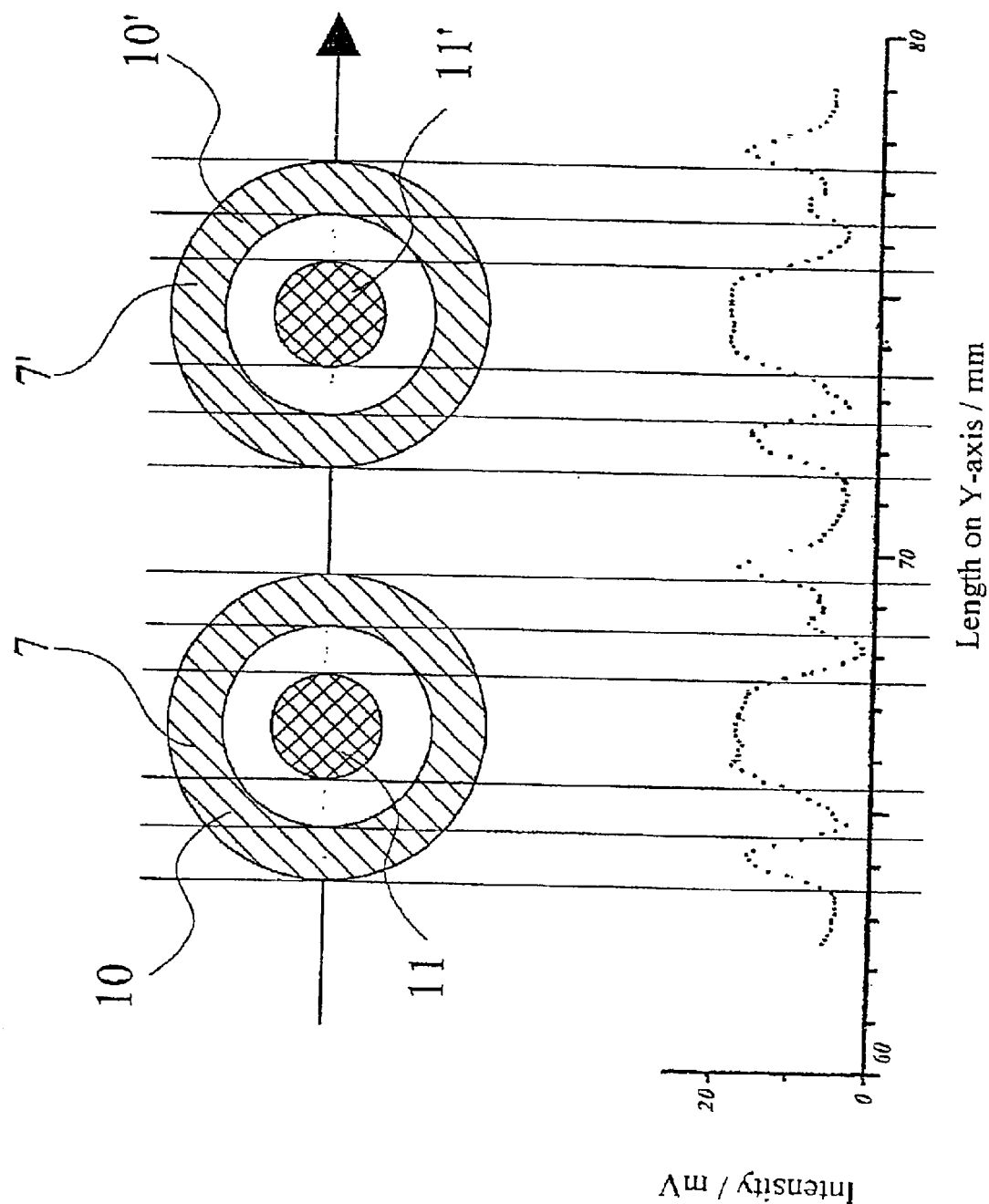

FIG. 6 shows a sequence of two measuring heads 7, 7', which are pushed through in the direction of the arrow with the measuring table 4 represented in FIG. 2, below an excitation light beam. The associated signals of the reflected light are represented in the lower portion of FIG. 6.

The measuring heads 7, 7' each have one silver electrode 10 or 10' respectively, which surrounds a cavity in an annular manner. Into this cavity is filled a membrane filling of an ion-selective membrane material 11, 11'. The ion-selective membrane material 11, 11' is contacted on the rear side, not shown here, of the measuring head with the silver electrode 10, 10' for derivation of the signals.

The membrane filling 11 or 11', while still in the liquid state before being filled into the cavity, was coloured with scarlet red in identical colorant concentration for both measuring heads 7, 7'.

As is clear in FIG. 6, not only do the coloured surfaces, coloured with scarlet red, of the membrane fillings 11, 11' absorb and reflect but so do the silver electrodes 10, 10'. This must be taken into account in the subsequent digital evaluation of the measured signals.

Nevertheless it can be clearly recognised that the membrane fillings 11, 11' generate a signal which has a plateau and which corresponds to the colorant concentration or the layer thickness of the membrane fillings 11, 11'. Furthermore it can be recognised that the plateaux of the signals of the membrane fillings 11, 11' have a ridge in which the intensity is slightly lower than at the edges of the plateaux. This can be traced back to the fact that, after filling, the membrane cocktail rises up the edge of the cavity. Thus in the middle of the membrane a surface is produced with less membrane cocktail, i.e. reduced layer thickness of the membrane fillings 11, 11'. This also proves that the method according to the invention is suitable for detecting layer thickness profiles and defects within the membrane and also on the membrane surface.

What is claimed is:

1. A method for detection of layer thickness or respective amount of filling, layer thickness distribution, defect, accumulation or inhomogeneity within a material layer, said material layer having a surface, comprising irradiating the surface layer with an electromagnetic radiation, and determining the amount of light emitted from the material layer, wherein the material of the layer is provided with an agent which absorbs the radiation, the material of the layer being mixed with the agent which absorbs the radiation before the layer is created.

2. The method according to claim 1, wherein the material of the layer is provided with the colouring agent as the agent which absorbs the radiation.

3. The method according to claim 2, wherein the colouring agent is a colorant or a pigment and/or with a UV absorber and/or with a fluorophore.

4. The method according to claim 1, wherein the layer is scanned with the electromagnetic radiation.

5. The method according to claim 4, wherein the layer is scanned point-by-point.

6. The method according to claim 4, wherein the layer is scanned in a linear manner with the electromagnetic radiation.

7. The method according to claim 1, wherein the electromagnetic radiation radiated onto the surface of the layer has a wavelength which corresponds to an absorption band of the agent which absorbs the radiation.

8. The method according to claim 1, wherein the electromagnetic radiation is ultraviolet and/or visible light.

9. The method according to claim 1, wherein the agent which absorbs the radiation is added to the material of the layer bonded to particles.

10. The method according to claim 1, wherein the agent which absorbs the radiation is added to the material of the layer bonded to latex particles.

11. The method according to claim 1, wherein curcumin, scarlet red and/or Sicodop blue are added to the material of the layer as the agents which absorb the radiation.

12. The method according to claim 1, wherein the material layer is a plastic membrane, a polymer membrane, an ion-selective membrane, or a hydrogel.

13. The method according to claim 1, wherein the material layer is an ion-selective membrane.

14. The method according to claim 1, wherein the light emitted is reflected radiation and/or fluorescent radiation.

* * * * *